United States Patent
Hah et al.

(10) Patent No.: US 8,551,759 B2
(45) Date of Patent: Oct. 8, 2013

(54) OLIGOMER PROBE ARRAY AND METHOD OF PRODUCING THE SAME

(75) Inventors: Jung-hwan Hah, Hwaseong-si (KR); Sung-min Chi, Hwaseong-si (KR); Kyoung-seon Kim, Suwon-si (KR); Won-sun Kim, Suwon-si (KR); Han-ku Cho, Seongnam-si (KR); Sang-jun Choi, Seoul (KR); Man-hyoung Ryoo, Hwaseong-si (KR)

(73) Assignee: Samsung Electronics Co., Ltd., Suwon-Si, Gyeonggi-Do (KR)

( * ) Notice: Subject to any disclaimer, the term of this patent is extended or adjusted under 35 U.S.C. 154(b) by 0 days.

(21) Appl. No.: 11/686,506

(22) Filed: Mar. 15, 2007

(65) Prior Publication Data
US 2008/0038732 A1 Feb. 14, 2008

(30) Foreign Application Priority Data
Jul. 31, 2006 (KR) .................... 10-2006-0072220

(51) Int. Cl.
*C12M 1/00* (2006.01)
*C12M 1/34* (2006.01)
*C12Q 1/68* (2006.01)
*G01N 33/53* (2006.01)
*G01N 33/551* (2006.01)
*G01N 33/552* (2006.01)
*G01N 33/545* (2006.01)
*C07H 21/02* (2006.01)

(52) U.S. Cl.
USPC ....... 435/283.1; 435/6.1; 435/7.1; 435/287.2; 436/524; 436/527; 436/531; 536/23.1

(58) Field of Classification Search
USPC ............. 435/6.1, 7.1, 283.1, 287.2; 436/524, 436/527, 531; 536/23.1; 977/773
See application file for complete search history.

(56) References Cited

U.S. PATENT DOCUMENTS

| 5,688,642 A * | 11/1997 | Chrisey et al. .................. 435/6 |
| 5,744,305 A | 4/1998 | Fodor et al. |
| 6,133,436 A * | 10/2000 | Koster et al. .................. 506/30 |
| 6,277,489 B1 * | 8/2001 | Abbott et al. .................. 506/15 |
| 2002/0072069 A1 | 6/2002 | Ford et al. |
| 2002/0123155 A1 * | 9/2002 | Himmelhaus et al. ........ 436/178 |
| 2003/0040129 A1 * | 2/2003 | Shah ............................ 436/526 |
| 2003/0044801 A1 * | 3/2003 | Harvey, III .................... 435/6 |
| 2004/0038229 A1 | 2/2004 | Keating et al. |
| 2004/0106110 A1 * | 6/2004 | Balasubramanian et al. .... 435/6 |
| 2005/0254998 A1 | 11/2005 | Nakamura et al. |

FOREIGN PATENT DOCUMENTS

| JP | 2002-111149 | 4/2002 |
| JP | 2005-007549 | 1/2005 |

OTHER PUBLICATIONS

Pritchard et al, Micron scale patterning of biological molecules, 1995, Angew. Chem. Int. Ed. Engl. 34, 91-93.*
Brinkely, A brief survey of methods for preparing protein conjugates with dyes, haptens and cross-linking reagents, 1992, Bioconjugate Chem., 3, 2-13.*
Bae et al, Selectively assembled Co nanoparticle stripes prepared by covalent linkage and microcontact printing, 2004, J. Phys. Chem. B, 108, 2575-2579.*
Joshi et al, Anhydrous silanization and antibody immobilization on hotwire CVD deposited silicon oxynitride films, IEEE India Annual Conference, INDICON, 2004, 1, 538-541.*
Kulkarni et al, Growth kinetics and thermodynamic stability of octadecyltrichlorosilane self assembled monolayer on Si (100) substrate, 2005, Materials Letters, 59, 3890-3895.*
Yang et al, Biomembrane mimetic surfaces by phospholipid self-assembled monolayers on silica substrates, 1999, Langmuir, 15, 1731-1737.*
English Abstract for Publication No. 2002-111149.
English Abstract for Publication No. 2005-007549.

* cited by examiner

*Primary Examiner* — Narayan Bhat
(74) *Attorney, Agent, or Firm* — F. Chau & Associates, LLC

(57) ABSTRACT

An oligomer probe array having improved reaction yield is provided. The oligomer probe array includes a substrate, an immobilization layer on the substrate, a plurality of nano particles coupled with a surface of the immobilization layer, and a plurality of oligomer probes coupled with surfaces of the nano particles.

31 Claims, 12 Drawing Sheets

OLIGOMER PROBE ARRAY AND METHOD OF PRODUCING THE SAME

CROSS REFERENCE TO RELATED APPLICATION

This application claims priority from Korean Patent Application No. 10-2006-0072220 filed on Jul. 31, 2006 in the Korean Intellectual Property Office, the contents of which are herein incorporated by reference in their entirety.

BACKGROUND OF THE INVENTION

1. Field of the Invention

The present disclosure is directed to an oligomer probe array and a method of producing the same and, more particularly, to an oligomer probe array including nano particles coupled with an oligomer probe and a method of producing the same.

2. Description of the Related Art

Currently, the advancements made in the genome project make it possible to establish genome nucleotide sequences of various organics. Accordingly, an interest in biopolymer microchips, particularly oligomer probe arrays, is growing. The oligomer probe arrays are extensively used to perform gene expression profiling and genotyping, to detect mutation and polymorphism such as SNP, to analyze proteins and peptides, to perform screening of potential drugs, and to develop and produce new drugs.

To develop the oligomer probe array, it is useful to efficiently realize the molecular interface between biomaterials and semiconductors such as silicon and to make the best use of intrinsic functions of the biomaterials. Particularly, in oligomer probe arrays such as DNA chips or protein chips, it is useful to immobilize related biomaterials in a predetermined region on a micrometer scale.

The type of genetic information ranges from genes to nucleotides, which are a minimum constituent unit of DNA and which may be analyzed using the oligomer probe array. Accordingly, the length scale of a probe cell is reduced to about ten μm to a few μm. Therefore, there is a demand for integration of the oligomer probe array so as to improve the reaction yield. Accordingly, a method of immobilizing a novel biomaterial is studied to satisfy the demand.

SUMMARY OF THE INVENTION

An embodiment of the present invention provides an oligomer probe array to improve a reaction yield.

An embodiment of the present invention provides a method of producing the oligomer probe array on a substrate.

According to an aspect of the present invention, there is provided an oligomer probe array including a substrate, an immobilization layer on the substrate, a plurality of nano particles coupled with a surface of the immobilization layer, and a plurality of oligomer probes coupled with surfaces of the nano particles.

According to another aspect of the present invention, there is provided a method of producing an oligomer probe array, the method including providing a substrate, forming an immobilization layer on a surface of the substrate, coupling a plurality of nano particles with a surface of the immobilization layer, and coupling a plurality of oligomer probes with surfaces of the nano particles.

BRIEF DESCRIPTION OF THE DRAWINGS

The above and other features of embodiments of the invention will become more apparent by describing in detail exemplary embodiments thereof with reference to the attached drawings.

DESCRIPTION OF THE EXEMPLARY EMBODIMENTS

Features of embodiments of the present invention and methods of accomplishing the same may be understood more readily by reference to the following detailed description of exemplary embodiments and the accompanying drawings. The present invention may, however, be embodied in many different forms and should not be construed as being limited to the embodiments set forth herein.

Hereinafter, a description will be given of oligomer probe arrays according to at least one embodiment of the invention with reference to the accompanying drawings.

Figure 1A:
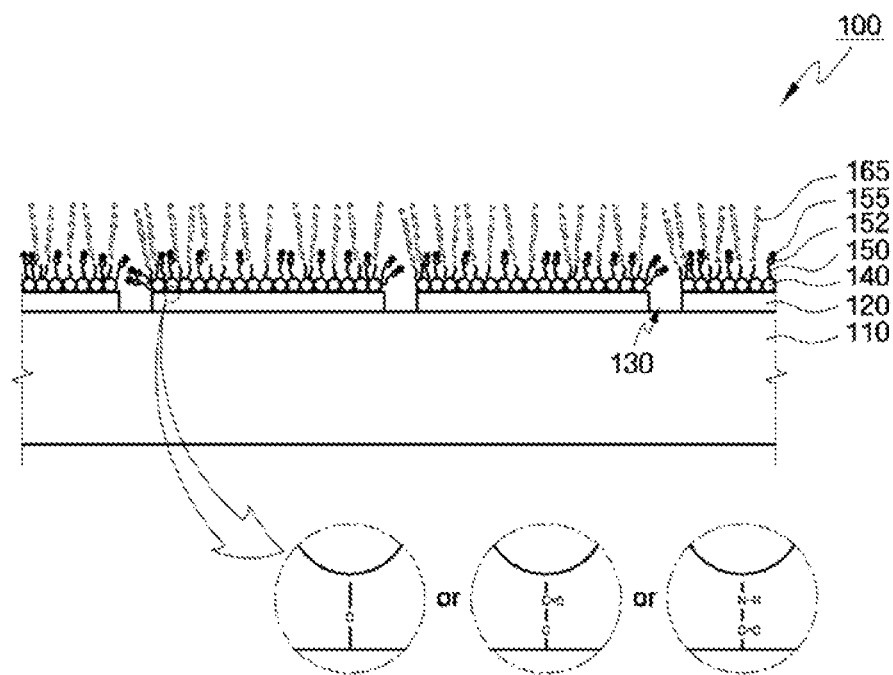
FIG. 1A is a sectional view of an oligomer probe array according to an embodiment of the invention.
Figure 1B:
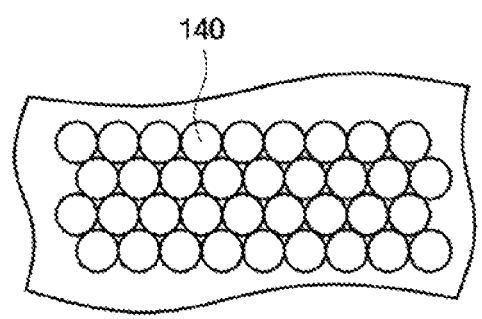
FIG. 1B is a plan view of a probe cell region of the oligomer probe array according to an embodiment of the invention.

First, a description will be given of an oligomer probe array according to an embodiment of the present invention. FIG. 1A is a sectional view of the oligomer probe array according to an embodiment of the present invention. FIG. 1B is a plan view of a probe cell region of the oligomer probe array according to an embodiment of the present invention.

Referring to FIG. 1, an oligomer probe array 100 includes a substrate 110, a probe cell region 120 on the substrate, a plurality of nano particles 140 coupled with the probe cell region 120, and a plurality of oligomer probes 165 coupled with surfaces of the nano particles 140.

The coupling may be a chemical bonding coupling, for example, a covalent bonding coupling. In detail, the coupling may be performed using covalent bonds that are formed through the reaction of functional groups in the probe cell region 120, the nano particles 140, linkers 150, and the oligomer probes 165 as described later.

The substrate 110 may be flexible or rigid. Examples of the flexible substrate include a membrane or plastic film formed of nylon or nitrocellulose. Examples of the rigid substrate include a silicon substrate or a transparent glass substrate formed of soda-lime glass. In the case of the silicon substrate or the transparent glass substrate, nonspecific bonding does not usually occur during a hybridization process. In addition, the silicon substrate or the transparent glass substrate can be manufactured by a process of producing various thin films and a photolithography process which are typically applied to a process of producing semiconductor devices or a process of producing LCD panels.

A plurality of probe cell regions 120 form an immobilization layer pattern, and are separated by probe cell separation regions 130.

The immobilization layer forming the probe cell region 120 includes functional groups on a surface thereof so as to be coupled with the nano particles 140. With respect to the hybridization analysis condition, a material that is not hydrolyzed but stable during contact to a phosphoric acid having the pH in the range of 6 to 9 or a TRIS buffer may be used. The immobilization layer may be formed of a silicon oxide film such as a PE-TEOS film, an HDP oxide film, a P—$SiH_4$ oxide film, or a thermal oxide film, silicates such as hafnium silicates and zirconium silicates, a metal oxynitride film such as a silicon oxynitride film, a hafnium oxynitride film, or a zirconium oxynitride film, a metal oxide film such as a titanium oxide film, a tantalum oxide film, an aluminum oxide film, a hafnium oxide film, a zirconium oxide film, or ITO, polyimides, polyamines, metal such as gold, silver, copper, and palladium, or polymers such as polystyrenes, polyacrylic acids, and polyvinyls. The production process may use materials that are stably used in the process of producing the semiconductors or the LCDs.

In the case of when the immobilization layer is formed of silicon oxide film or silicate or silicon oxynitride film, the coupling groups of the nano particles 140 may include silicon groups that are reacted with Si(OH) groups of the surface of the immobilization layer to form siloxane (Si—O) bonds.

For example, the coupling group may include a —Si(OMe)$_3$, —SiMe(OMe)$_2$, —SiMeCl$_2$, —SiMe(OEt)$_2$, —SiCl$_3$, or —Si(OEt)$_3$ group. Examples of a material having the functional group 150 and a silicon group capable of forming the siloxane bond include N-(3-(triethoxysilyl)-propyl)-4-hydroxybutyramide, N,N-bis(hydroxyethyl) aminopropyl-triethoxysilane, acetoxypropyl-triethoxysilane, 3-glycidoxy propyltrimethoxysilane, and the silicon compound disclosed in U.S. Pat. No. 6,262,216, the contents of which are incorporated herein by reference in their entirety.

In the case of when the immobilization layer is formed of a metal oxide film, the coupling groups of the nano particles 140 may include metal alkoxide or metal carboxylate groups.

In the case of when the immobilization layer is formed of a silicon nitride film, a silicon oxynitride film, a metal oxynitride film, polyimides, or polyamines, the coupling groups of the nano particles 140 may include anhydride, hydrochloric acid, alkyl halide, or chlorocarbonate groups.

In the case of when the probe cell region 120 is formed of metal, the coupling groups of the nano particles 140 may include sulfide, selenide, arsenide, telluride, or antimonide groups.

In the case of when the probe cell region 120 is formed of a polymer, the coupling groups of the nano particles 140 may include acryl, styryl, or vinyl groups.

The probe cell separation region 130 includes an inactive region which surrounds the probe cell region 120 and is not coupled with the nano particle. In the oligomer probe array 100 according to an embodiment of the present invention, the surface of the substrate 110 is directly exposed. As a result, since it is possible to prevent undesired coupling of the nano particles 140, the undesired noise resulting from the coupling of the oligomer probe does not usually occur.

The probe cell regions 120 are separated from each other by the probe cell separation regions 130. Oligomer probes 165 having the same sequence may be coupled through the nano particles 140 with the single probe cell region 120. Oligomer probes 165 having different sequences may be coupled through the nano particles 140 with the different probe cell regions 120. The functional group remaining on the surface of the probe cell region 120 may be inactively capped by a capping group. Examples of capping include acetylation.

The nano particle 140 have a size substantially in nanometers range. The nano particle 140 may act as a support. Examples of a substance of the nano particles 140 include, but are not limited to, polystyrene or silica. The nano particle 140 may be a spherical bead having a diameter in the range of 10 to 1,000 nm, particularly 50 to 500 nm. The shape of the nano particle is not limited to the sphere, and may be rectangular or conic.

The nano particle 140 according to an embodiment of the present invention connects the probe cell region 120 of the immobilization layer to the oligomer probe 165. The functional group of the nano particle 140 may have a functional group capable of being coupled with the immobilization layer, a functional group capable of being coupled with the linker 150 in the case of when the linkers 150 are interposed, and a functional group capable of being coupled with the oligomer probes 165 in the case of when the linkers 150 are not interposed on the surface thereof. The three functional groups may be the same or different. Examples of the functional group include, but are not limited to, a hydroxyl group, a carboxyl group, an amine group, a halo group, and a sulfonate group.

The coupling of the nano particles 140 and the probe cell region 120 may be via covalent bonding. Therefore, the nano particles 140 may be fixed to the immobilization layer, that is, the probe cell region 120 using stronger bonding in comparison with the case of when electrostatic force or capillary force is used. In the case of when the nano particles 140 are coupled, it is apparent to those skilled in the art that the functional group of the nano particle 140 is converted into an ether bond, an ester bond, or a peptide amide bond. The functional group which remains on the surface of the nano particle 140 may be inactively capped by a capping group. Examples of the capping include acetylation.

The probe cell region 120 of the immobilization layer coupled with the nano particles 140 may be a self assembled single molecular layer. The nano particles 140 may be randomly arranged on the probe cell region 120. However, in the case of when the nano particles are regularly fixed to the immobilization layer as shown in FIG. 1B, the surface area that is capable of being coupled with the oligomer probe is increased. As a result, the reaction yield of the oligomer probe array is increased.

The linker 150 includes a functional group that is capable of being simultaneously coupled with the nano particle 140 and the oligomer probe 165. An end of the linker 150 is coupled with the nano particle 140, and another end of the linker 150 is coupled with the oligomer probe 165. The linker 150 provides a spatial margin, so that the oligomer probe array 100 freely interacts with the target sample, for example, so that hybridization occurs. Accordingly, the linker molecule 150 may have length that is sufficient to achieve free interaction between the oligomer probe 165 and the target sample, for example, a length of 6 to 50 atoms. In the case of when the spatial margin is desirably assured to achieve the hybridization, the linker 150 may be removed.

Meanwhile, an oligo nucleic acid may be used as the linker 150. The oligo nucleic acid is used to assure the spatial margin so that a nucleic acid of 1 to 5 mer firstly coupled with the functional group of the nano particle 140 is not hybridized. Needless to say, the length of the oligo nucleic acid which is used as the linker 150 is not limited to the range of 1 to 5 mer.

The functional group which remains on the surface of the nano particle 140 may be inactively capped by a capping group 155. After the desired coupling is finished, the remaining functional group is deactivated by the capping group 155. Examples of the capping include acetylation.

The oligomer probe 165 is a polymer that is formed of two or more monomers covalently bonded to each other and has a molecular weight of about 1000 or less. However, the molecular weight is not limited to the above numerical value. The oligomer may include 2 to 500 monomers, or 5 to 30 monomers. Examples of the monomers may include nucleosides, nucleotides, amino acids, or peptides according to the type of probe fixed to the oligomer probe array.

In the case of when the linker is interposed, the oligomer probe 165 is coupled with the functional group 152 of the linker 150, and the linker 150 is connected by the nano particle 140 to the probe cell region 120. In the case of when the linker is not interposed, the oligomer probe 165 is directly coupled with the nano particle 140, and the nano particle 140 is fixed to the probe cell region 120.

Nucleosides and nucleotides may include a known purine or pyrimidine base, or include methylated purine or pyrimidine, or acylated purine or pyrimidine. Furthermore, nucleosides and nucleotides may include known ribose or deoxyribose saccharides, or include modified saccharides in which one or more hydroxyl groups are substituted by halogen atoms or aliphatics or to which a functional group such as ether or amine is bonded.

The amino acid may be an L-, D-, or nonchiral-type amino acid which is found in nature. Alternatively, the amino acid may be a modified amino acid or an analog of the amino acid.

The peptide is a compound that is formed by amide bonding between a carboxyl group of an amino acid and an amino group of another amino acid.

The oligomer probe 165 may be formed of two or more nucleosides, nucleotides, amino acids, or peptides.

In an embodiment of the present invention, a description is given of the oligomer probe array 100 in the case of when an amino silane coupling agent is not used. An oligomer probe array may be provided where the nano particles 140 are coupled with the probe cell region 120 even though the amino silane coupling agent is used.

In addition, the silane coupling agent, which is not shown, may be further formed between the immobilization layer and the nano particles 140. The silane coupling agent may be a substance that forms a self-aligned film of a single molecular layer in the case of when an amino silane compound is used to form the immobilization layer of the substrate 110. The silane coupling agent may be a substance that includes a functional group capable of being coupled with the nano particle 140, the linker 150, or the oligomer 165, and may be applied on the surface of the immobilization layer. The above-description will be identically applied to the oligomer probe arrays 101 to 106 as shown in FIGS. 2 to 7.

Figure 2:
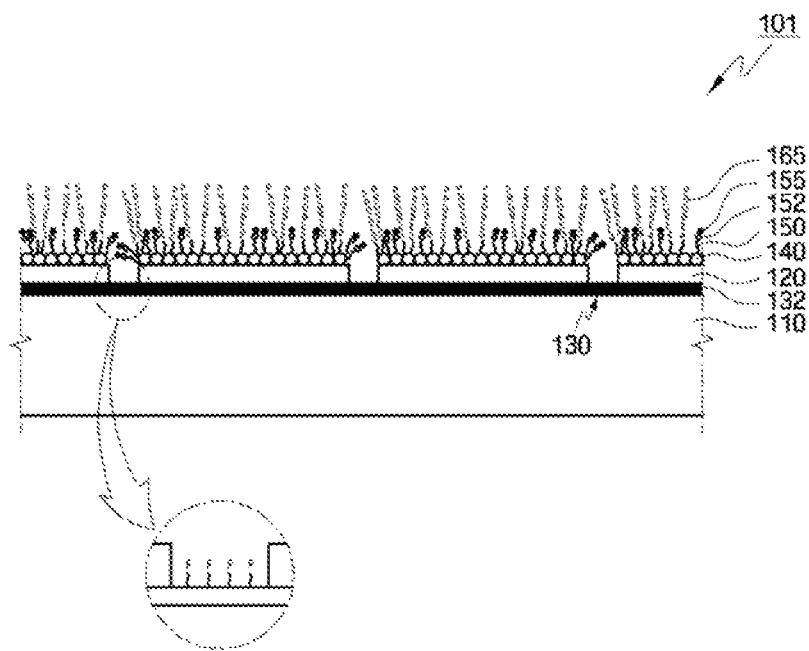
FIG. 2 is a sectional view of an oligomer probe array according to another embodiment of the invention.

FIG. 2 is a sectional view of an oligomer probe array according to another embodiment of the present invention.

Referring to FIG. 2, an oligomer probe array 101 according to the present embodiment includes a coupling blocking film 132 that is formed on an entire surface of a substrate 110, and is different from that of the embodiment of FIG. 1 in that a probe cell region 120 is not directly formed on the substrate 110 but on a coupling blocking film 132. The coupling blocking film 132 is exposed to a probe cell separation region 130. The coupling blocking film 132 may be formed of fluorides containing a fluorine group like a fluorosilane film. Furthermore, the coupling blocking film 132 may be a silicide film, a polysilicon film, or an epitaxial film formed of Si or SiGe. In the present embodiment, since there is no functional group to be coupled with nano particles 140 in the probe cell separation region 130 due to the coupling blocking film 132, the occurrence of noise may be prevented.

Figure 3:
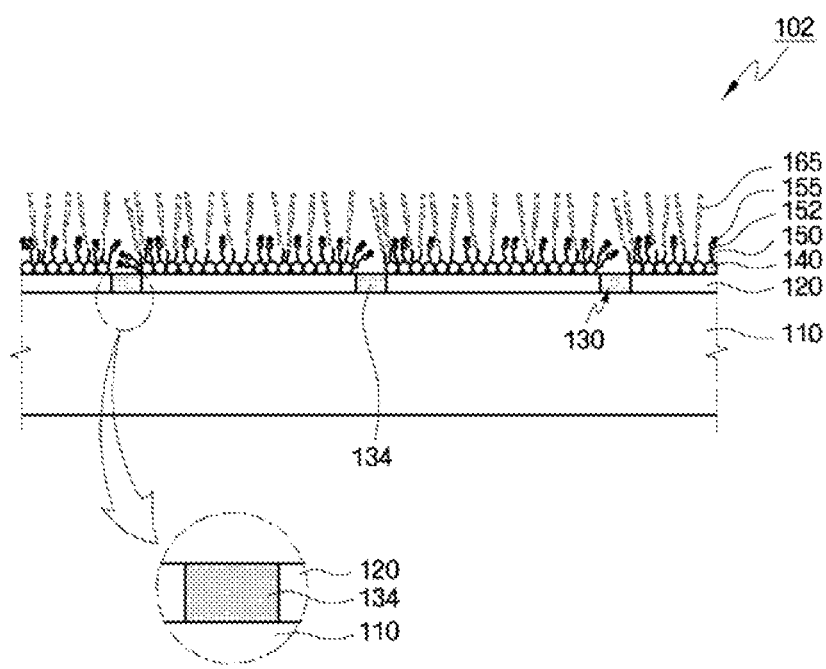
FIG. 3 is a sectional view of an oligomer probe array according to another embodiment of the invention.

FIG. 3 is a sectional view of an oligomer probe array according to another embodiment of the present invention.

Referring to FIG. 3, an oligomer probe array 102 according to the present embodiment is different from that of the embodiment of FIG. 1 in that a coupling blocking filling material 134 having the coupling blocking property of an oligomer probe 165 or a monomer is filled in a probe cell separation region 130. The coupling blocking filling material 134 may be formed of fluorides containing a fluorine group or may be a polysilicon film. In the present embodiment, since the probe cell separation region 130 is filled with the coupling blocking filling material 134 such that the functional group to be coupled with nano particles 140 is not present on the surface of the region, the occurrence of noise may be prevented.

Figure 4:
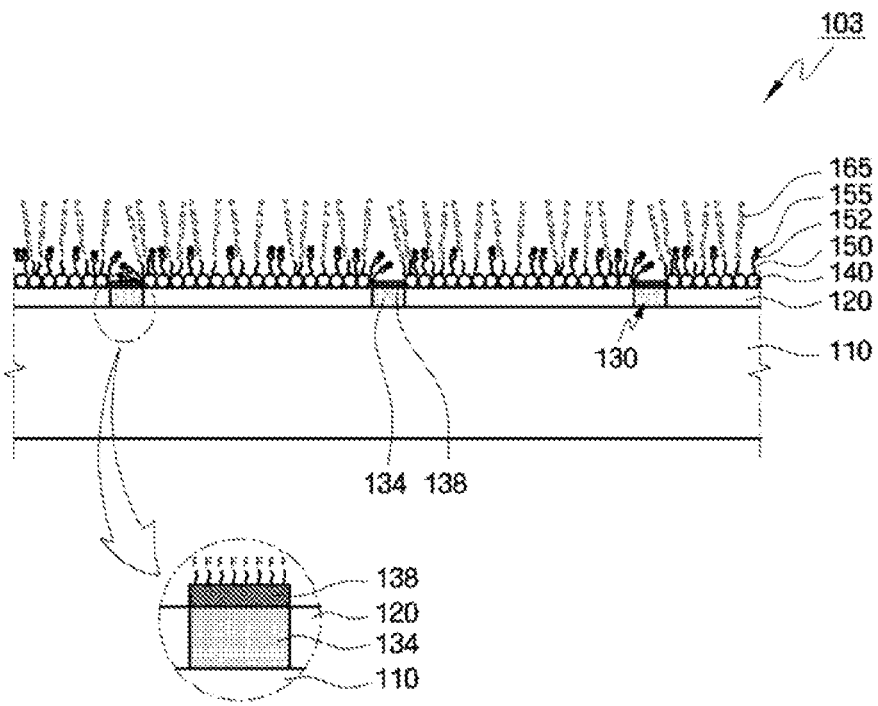
FIG. 4 is a sectional view of an oligomer probe array according to another embodiment of the invention.

FIG. 4 is a sectional view of an oligomer probe array according to another embodiment of the present invention.

With reference to FIG. 4, in an oligomer probe array 103 according to the present embodiment, a filling material 134 is filled in probe cell separation regions 130 between probe cell regions 120, and coupling blocking films 138 are formed on the filling material. In this case, it is unnecessary for the filling material 134 to have the coupling blocking property. In the present embodiment, since the probe cell separation regions 130 are covered with the filling material 134 and the coupling blocking films 138, such that the functional group to be coupled with nano particles 140 is not present on the surface of the region, the occurrence of noise may be prevented.

Figure 5:
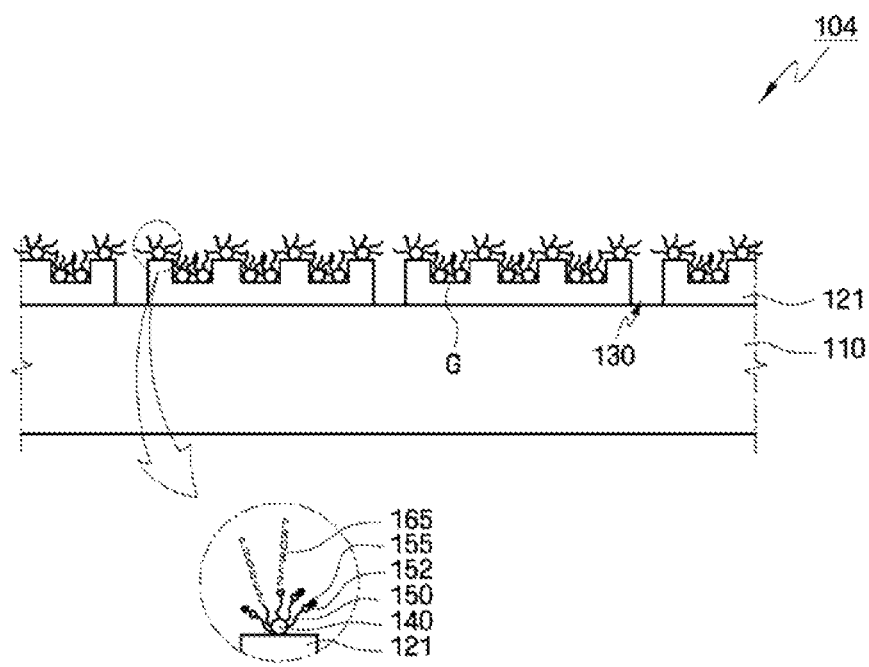
FIG. 5 is a sectional view of an oligomer probe array according to another embodiment of the invention.

FIG. 5 is a sectional view of an oligomer probe array according to another embodiment of the present invention.

With reference to FIG. 5, an oligomer probe array 104 according to the present embodiment is different from that of the embodiment of FIG. 1 in that a probe cell region 121 has a three-dimensional surface. In connection with this, the three-dimensional surface means that the surface of the probe cell region 121 has a three-dimensional structure due to one or more grooves (G) formed in the probe cell region 121. Needless to say, the structure is not limited to the structure including the grooves as long as the surface has a three-dimensional structure. The three-dimensional surface increases the area coupled with nano particles 140 in comparison with the oligomer probe array to which the same rule of design is applied, thus increasing the area to be coupled with an oligomer probe 165. Accordingly, it is possible to increase detection intensity as compared to the oligomer probe array to which the same rule of design is applied.

Additionally, in a combined embodiment of the above-mentioned embodiments, the probe cell regions 120 of the oligomer probe arrays 101, 102, and 103 shown in FIGS. 2 to 4 may have the three-dimensional surfaces as shown in FIG. 5.

Figure 6:
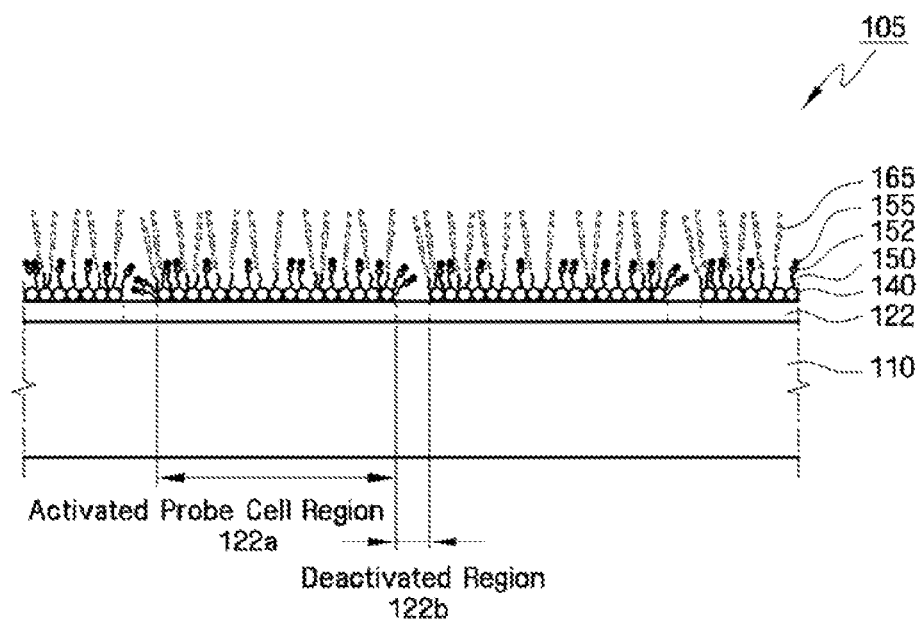
FIG. 6 is a sectional view of an oligomer probe array according to another embodiment of the invention.

FIG. 6 is a sectional view of an oligomer probe array according to another embodiment of the present invention.

With reference to FIG. 6, an oligomer probe array 105 according to the present embodiment is different from that of the embodiment of FIG. 1 in that an immobilization layer 122 is not divided.

In detail, the immobilization layer 122 that is formed on a substrate includes a plurality of activated probe cell regions 122a coupled with a plurality of nano particles 140, and deactivated regions 122b that surround the activated probe cell regions and are not coupled with the nano particles 140. The activated probe cell regions 122a may be coupled with the nano particles 140.

In view of functionality, the activated probe cell region is substantially the same as the probe cell region of FIG. 1 (see reference numeral 120 of FIG. 1), and the deactivated region is substantially the same as the probe cell separation region of FIG. 1 (see reference numeral 130 of FIG. 1).

However, in the case of the deactivated region 122b, since the immobilization layer 122 is included unlike FIG. 1, the functional group of the surface of the immobilization layer may be present on the surface of the region. Thus, it is necessary to block the action of the functional group. The functional group of the deactivated region 122b may be inactively capped by a capping group.

Figure 7:
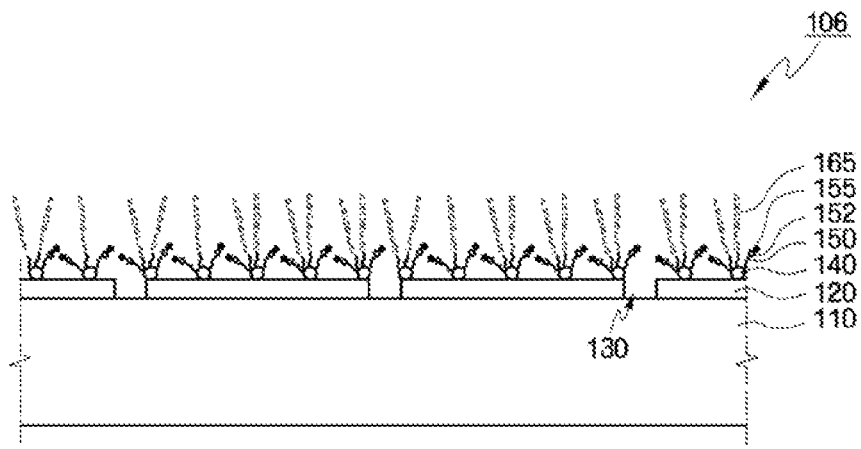
FIG. 7 is a sectional view of an oligomer probe array according to another embodiment of the invention.

FIG. 7 is a sectional view of an oligomer probe array according to another embodiment of the present invention.

With reference to FIG. 7, an oligomer probe array 106 according to the present embodiment is different from that of the embodiment of FIG. 1 in that nano particles 140 do not form a two-dimensional self assembled single molecular film but are randomly arranged. It is possible to achieve various types of combinations of the embodiments of FIGS. 2 to 6. In connection with this, the production process may be simpler in comparison with the case of when the nano particles 140 are arranged to form the self assembled single molecular film as shown in FIGS. 1 to 6.

Hereinafter, a description will be given of a method of producing the oligomer probe arrays according to the embodiments of the present invention with reference to FIGS. 1 to 7 and FIGS. 8A to 13B.

FIGS. 8A to 8J are sectional views of structures at the middle steps of a procedure which illustrates the production of the oligomer probe array according to an embodiment of the present invention shown in FIG. 1.

Figure 8A:
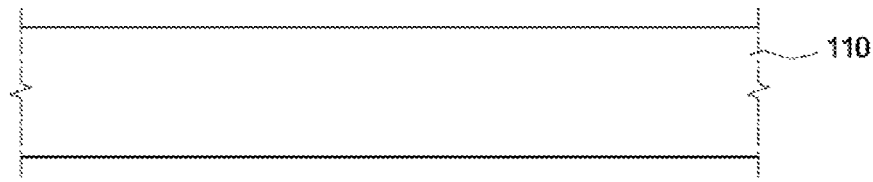
FIGS. 8A to 8J are sectional views of structures at the middle steps of a procedure which illustrates the production of the oligomer probe array according to an embodiment of the invention shown in FIG. 6.
Figure 8B:
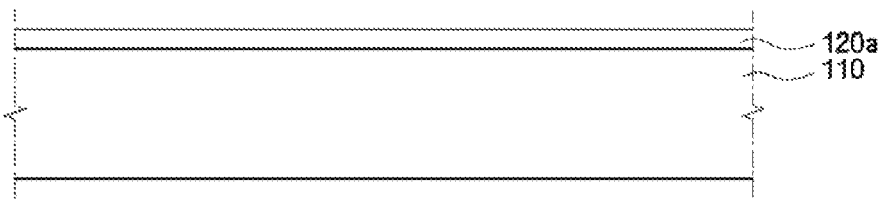
Figure 8C:
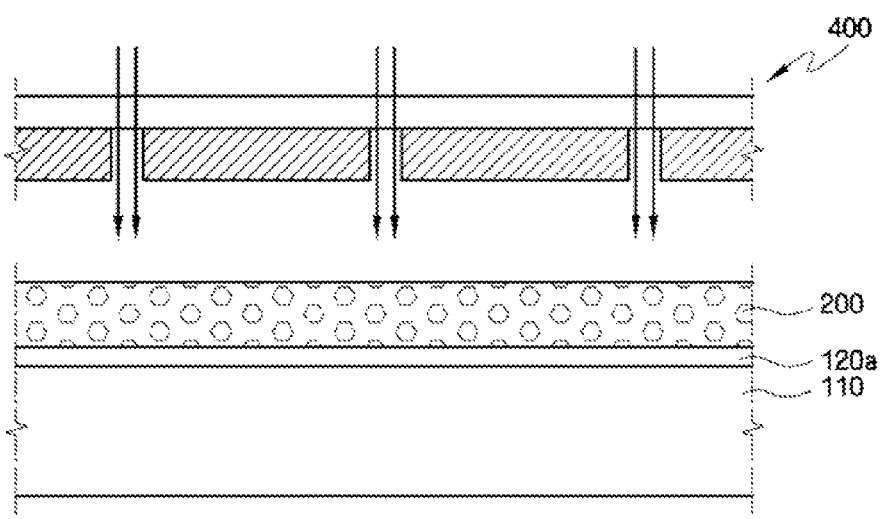

With reference to FIGS. 1, 8A, and 8B, an immobilization layer 120a is formed on a substrate 110. The immobilization layer 120a may be formed of a silicon oxide film such as a PE-TEOS film, an HDP oxide film, a P—$SiH_4$ oxide film, or a thermal oxide film, silicates such as hafnium silicates and zirconium silicates, a metal oxynitride film such as a silicon oxynitride film, a hafnium oxynitride film, or a zirconium oxynitride film, a metal oxide film such as a titanium oxide film, a tantalum oxide film, an aluminum oxide film, a hafnium oxide film, a zirconium oxide film, or ITO, polyimides, polyamines, metal such as gold, silver, copper, and palladium, or polymers such as polystyrenes, polyacrylic acids, or polyvinyls.

A deposition process that is stably used in a process of producing semiconductors or a process of producing LCDs, for example, CVD (chemical vapor deposition), SACVD (sub-atmospheric chemical vapor deposition), LPCVD (low pressure chemical vapor deposition), PECVD (plasma enhanced chemical vapor deposition), sputtering, or spin coating, may be used, and a substance that, is capable of being stably formed on the substrate 110 is used. After a photoresist film 200 is formed on a film 120a for forming the probe cell region, the photoresist film 200 is exposed in a projection exposing device using a photomask 400 which defines the probe cell region. Examples of the photomask 400 which defines the probe cell region include a mask in which a light blocking pattern defining the probe cell region is formed on a transparent substrate to form a checkerboard-type exposure region. The shape of the light blocking pattern may be changed according to the type of the photoresist film used.

Figure 8D:
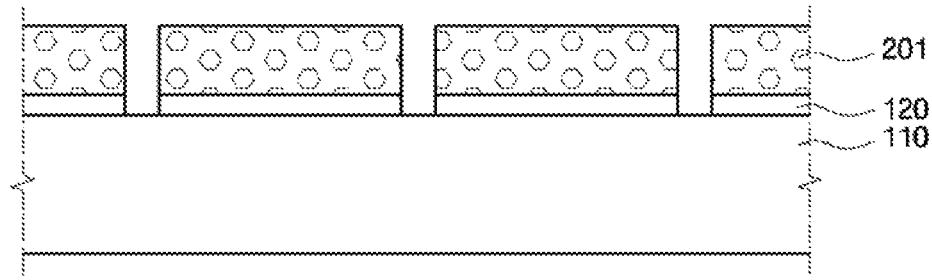
Figure 8E:
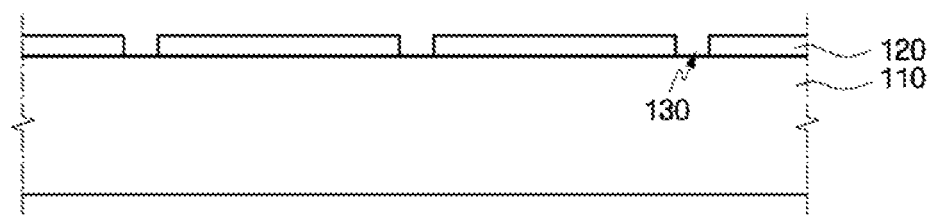

With reference to FIG. 8D, after the exposed photoresist film is developed to form a photoresist pattern 201, the film 120a for forming the probe cell region is etched using the resulting photoresist film as an etching mask to form the probe cell region 120. Next, as shown in FIG. 8E, the photoresist pattern 201 is removed to complete the production of the probe cell region 120.

Hereinafter, the probe cell region 120 that is formed of the silicon oxide film will be described. The SiOH group that is capable of being coupled with the oligomer probe is exposed on the surface of the probe cell region 120 that is formed of the silicon oxide film.

Figure 8F:
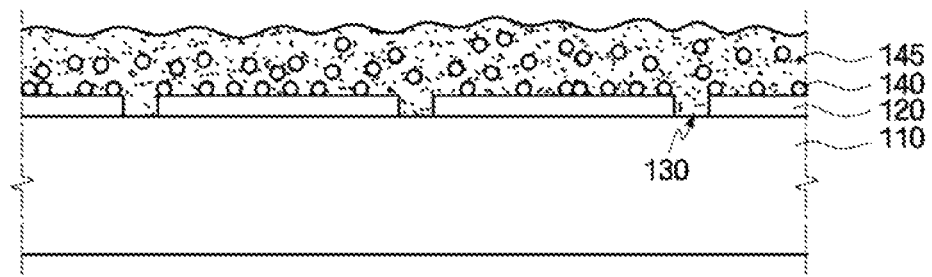

As shown in FIG. 8F, a suspension solution 145 containing nano particles 140 is dispensed on the probe cell region 120. Typical examples of the nano particles 140 may include polystyrene beads, and examples of the dispensing may include spin coating.

Figure 8G:
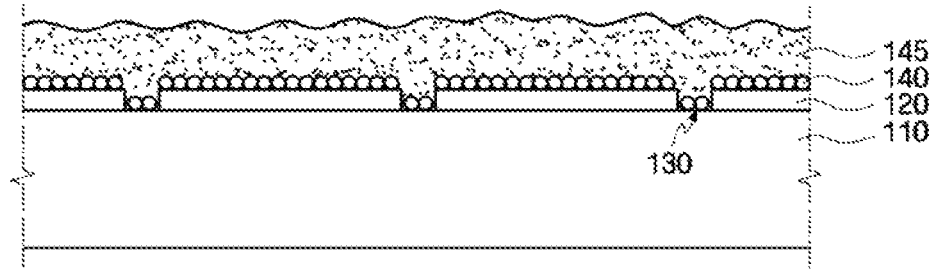

After the dispensing, as shown in FIG. 8G, the nano particles 140 are arranged on the probe cell region 120. The particles may be arranged to form a self assembled single molecular film on the surface of the probe cell region 120. The functional groups that are present in the nano particles 140 are coupled with the probe cell regions 120. The nano particles 140 may be present in the probe cell separation regions 130. However, since there are no functional groups capable of being coupled with the nano particles 140 in the probe cell separation regions 130, the nano particles 140 are removed from the probe cell separation regions 130 during the subsequent process.

Figure 8H:
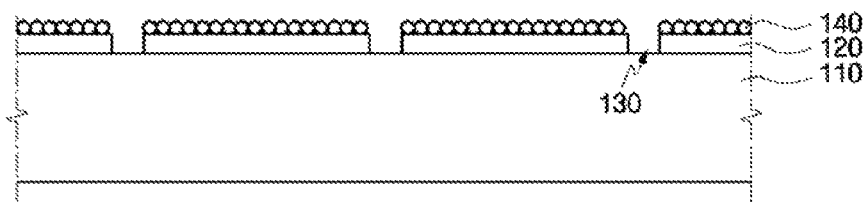

With reference to FIG. 8H, washing and curing processes may be performed to arrange the nano particles 140 on only the probe cell regions 120.

Figure 8I:
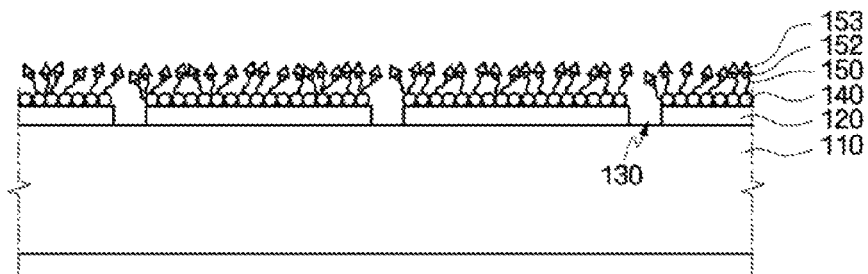

As shown in FIG. 8I, linkers 150 which are connected to protective groups 153 are coupled with the nano particles 140 which are coupled with the surfaces of the probe cell regions 120. Phosphoamidite may be used as the linker 150 that protects the functional groups 152 of the linkers using the protective groups 153.

A protective group is a group that prevents attachment sites from participating in a chemical reaction, and deprotecting means that the protective groups are separated from the attachment sites so that the sites participate in the chemical reaction. For example, an acid labile or photo labile protective group is present in the functional group 152 coupled with the linker 150. For example, the photo labile protective group 153 may be selected from various types of positive photo labile groups containing nitroaromatic compounds such as o-nitrobenzyl derivatives or benzylsulfonyl. Examples of the photo labile protective group 152 may include 6-nitroveratryloxycarbonyl (NVOC), 2-nitrobenzyloxycarbonyl (NBGC), α, α-dimethyl-dimethoxybenzyloxycarbonyl (DDZ), or dimethoxytrityl (DMT).

After coupling with the linkers 150, the functional groups 152 which are exposed on the surface and are not coupled with the linkers 150 are inactively capped using capping groups 155 to prevent noise from the oligomer probe. Examples of capping include acetylation.

Figure 8J:
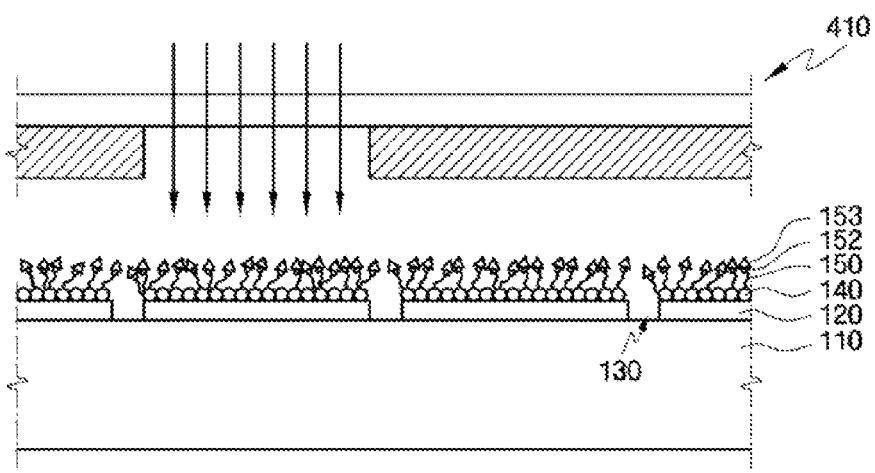

With reference to FIG. 8J, in order to perform the in situ synthesis of the oligomer probe, the photo labile protective group 153 that is coupled with the functional group 140 of the end of the linker 150 is deprotected using a mask 410 which exposes the desired probe cell region 120.

A desired oligomer probe, which is not shown, may be coupled with the exposed functional group. In the case of when an oligonucleotide probe is synthesized using in situ photolithography, the nucleotide phosphoamidite monomer which is bonded to the photo labile protective group 153 is coupled with the exposed functional group 140, and the functional group that does not participate in the coupling is inactively capped, and oxidation is performed to convert a phosphite triester structure which is formed by bonding between phosphoamidite and 5'-hydroxy group into a phosphate structure. As described above, the deprotection of the desired probe cell region 120, the coupling of the monomers having the desired sequence, the inactive capping of the functional group which does not participate in the coupling, and the oxidation to achieve conversion into the phosphate structure may be sequentially repeated to synthesize oligonucleotide probes having the desired sequence according to the probe cell regions 120.

The coupling of the oligomer probe may be performed using a spotting process, a piezoelectric printing process, or a micropipetting process instead of the above-mentioned photolithography process.

FIGS. 9A to 9D are sectional views of structures at the middle steps of a procedure which illustrates the production of the oligomer probe array according to an embodiment of the present invention shown in FIG. 6.

A description will be given of a method of producing the micro array of FIG. 6 with reference to FIGS. 6, 8A to 8H, and 9A and 9B.

First, an immobilization layer 122 is formed on a substrate 110 through the procedure shown in FIGS. 8A and 8B.

Figure 9A:
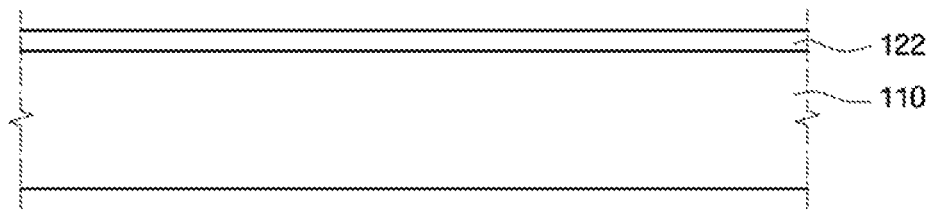
FIGS. 9A to 9D are sectional views of structures at the middle steps of a procedure which illustrates the production of the oligomer probe array according to another embodiment of the invention shown in FIG. 1.
Figure 9B:
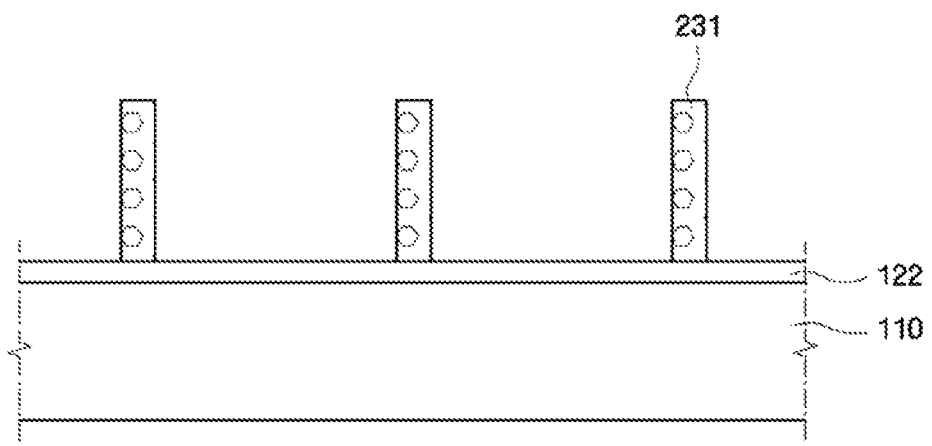

With reference to FIG. 9B, a photoresist film is formed on the immobilization layer 122, exposed, and developed to form photoresist walls 231.

Figure 9C:
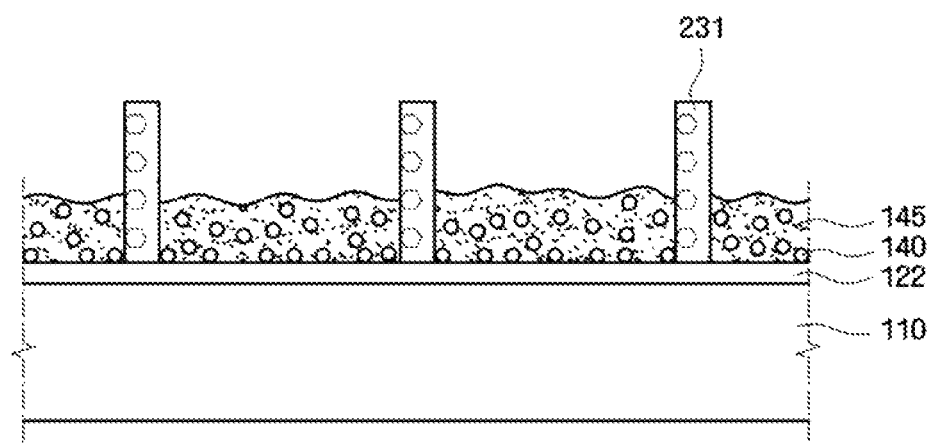

With reference to FIG. 9C, a suspension solution 145 containing nano particles 140 is dispensed on an entire surface of the substrate on which the photoresist walls 231 are formed.

Figure 9D:
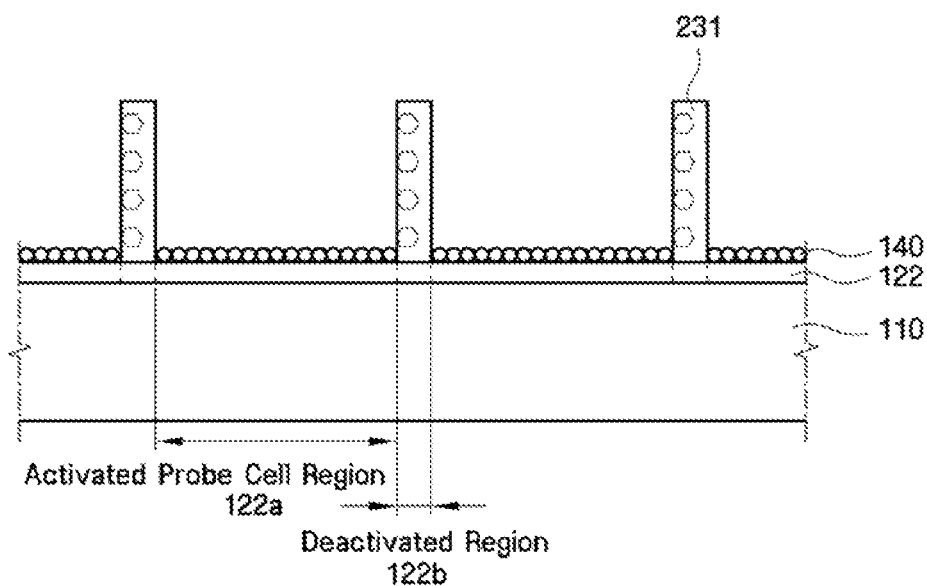

With reference to FIG. 9D, the dispensing, washing and curing processes are performed to arrange the nano particles 140 on the immobilization layer 122 that is exposed to the photoresist walls 231. Since the photoresist wails 231 act as physical barriers during the arrangement of the nano particles 140, it is easy to achieve a uniform arrangement of the nano particles 140. The nano particles 140 may form a self assembled single molecular film. As a result, the immobilization layer 122 may be divided into an activated probe cell region 122a which is coupled with the nano particle 140, and a deactivated region 122b which surrounds the activated probe cell region 122a.

Next, linkers, which are not shown, are coupled with the nano particles 140, the photoresist walls 231 are removed, and the oligomer probe is coupled using an in situ photolithography process, a spotting process, a piezoelectric printing process, or a micropipetting process.

However, if the nano particles 140 have functional groups capable of being coupled with the oligomers or the monomers and provide a spatial margin required during hybridization with a target sample during a subsequent hybridization process, immediately after the coupling of the nano particles 140, the photoresist walls 231 are removed, and the oligomer probe is coupled using an in situ photolithography process, a spotting process, a piezoelectric printing process, or a micropipetting process.

In addition, in the case of when the photoresist wails 231 are not used, the formation of a photoresist pattern on the immobilization layer 122, the selective capping of the exposed immobilization layer by the photoresist pattern, the removal of the photoresist pattern, and the coupling of the nano particles 140 may be sequentially performed to form the activated region 122a which is coupled with the nano particles 140 and the capped deactivated region 122b. This is not shown in the drawing.

Through the above-mentioned description, the method of producing the oligomer probe array 105 according to an embodiment of the present invention shown in FIG. 6 using the photoresist wall 231 is disclosed. However, the use of photoresist wall 231 is not limited thereto, but the photoresist wall 231 may be used to produce the oligomer probe arrays 100 to 104, and 106 according to at least one embodiment as shown in FIGS. 1 to 5, and 7.

Figure 10A:
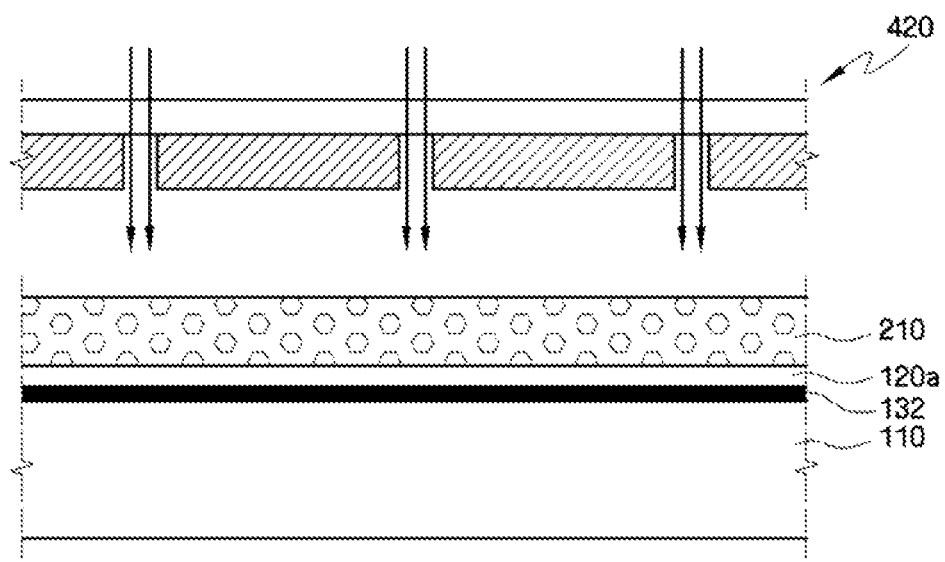
FIGS. 10A and 10B are sectional views of structures at the middle steps of a procedure which illustrates the production of the oligomer probe array according to another embodiment of the invention shown in FIG. 2.
Figure 10B:
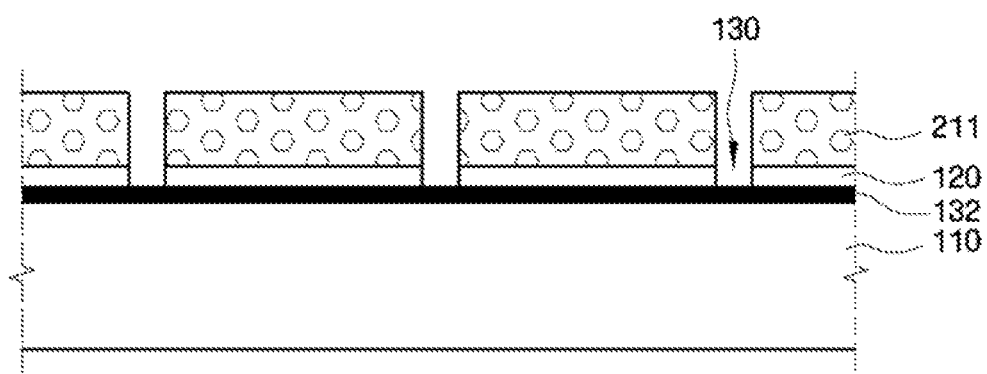

FIGS. 10A and 10B are sectional views of structures at the middle steps of a procedure which illustrates the production of the oligomer probe array according to an embodiment of the present invention shown in FIG. 2.

With reference to FIG. 10A, a coupling blocking film 132, an immobilization layer 120a, and a photoresist film 210 are sequentially formed on a substrate 110. Subsequently; the photoresist film 210 is exposed using a photomask 420 which defines a probe cell region 120.

With reference to FIG. 10B, after the exposed photoresist film 210 is developed to form a photoresist pattern 211, the immobilization layer 120a is etched using the resulting photoresist film using an etching mask to form the probe cell regions 120, a portion of the coupling blocking film 132 between the probe cell regions 120 is exposed to define the probe cell separation regions 130. Subsequent processes are substantially the same as those of FIGS. 8E to 8H.

Figure 11:
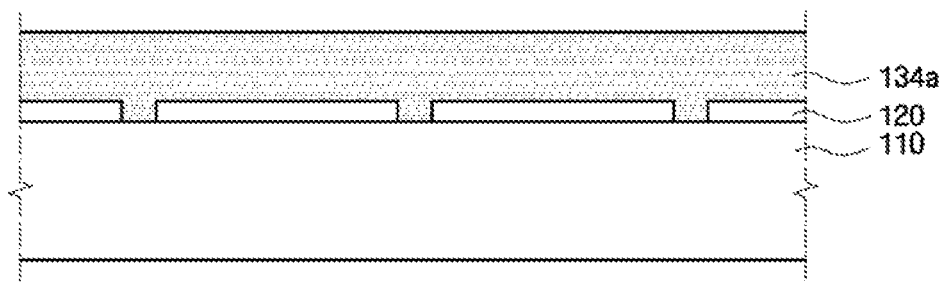
FIG. 11 is a sectional view of a structure at a middle step of a procedure which illustrates the production of the oligomer probe array according to another embodiment of the invention shown in FIG. 3.

FIG. 11 is a sectional view of a structure at a middle step of a procedure which illustrates the production of the oligomer probe array according to an embodiment of the present invention shown in FIG. 3.

With reference to FIG. 11, after probe cell regions 120 are formed as shown in FIGS. 8A to 8B, a filling film 134a is formed to till gaps between the regions 120. The filling film 134a has the blocking property with respect to the coupling of the oligomer. The filling film may be a film having excellent gap filling property that is formed of, for example, fluorosilane or polysilicon.

Subsequently, the filling film 134a is planarized using chemical mechanical polishing or etch back, which is not shown, to expose the surface of the probe cell region 120, thereby producing a coupling blocking filling material 134 of the oligomer probe 165 which fills the gaps between the probe cell regions 120, as shown in FIG. 3.

Figure 12:
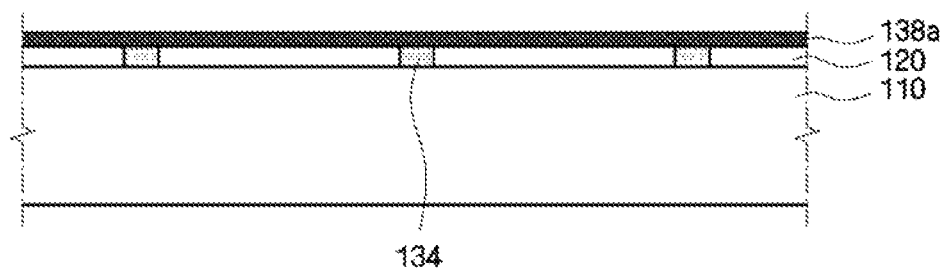
FIG. 12 is a sectional view of a structure at a middle step of a procedure which illustrates the production of the oligomer probe array according to another embodiment of the invention shown in FIG. 4.

FIG. 12 is a sectional view of a structure at a middle step of a procedure which illustrates the production of the oligomer probe array according to an embodiment of the present invention shown in FIG. 4.

With reference to FIG. 12, after probe cell regions 120 are formed as shown in FIGS. 8A to 8E, a filling material 134 is formed to fill gaps between the regions 120. Subsequently, a coupling blocking film 138a is formed on an entire surface of a substrate 100.

Next, the coupling blocking film 138a that is formed on an upper side of the probe cell region 120 is selectively removed to complete the production of the filling material 134 and the coupling blocking film 138 on the filling material. This is not shown. After a polysilicon film or an epitaxial film including Si or SiGe is formed using the filling material 134, the coupling blocking film 138a is formed using a metal film formed of Co, Ni, or Ti, a silicidation process is performed, and the unreacted metal film is removed to form the coupling blocking film 138a only on the upper side of the filling material 134, as shown in FIG. 4.

Figure 13A:
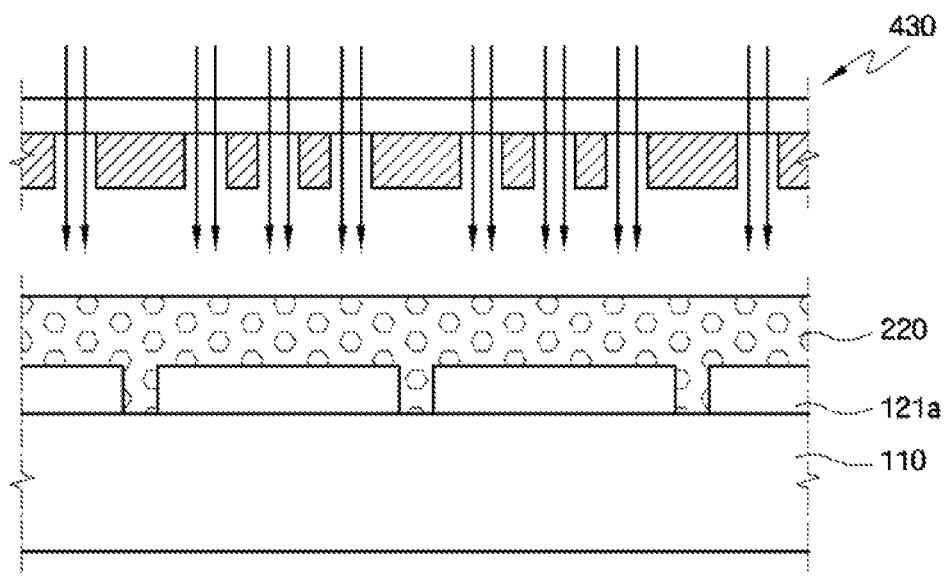
FIGS. 13A and 13B are sectional views of structures at the middle steps of a procedure which illustrates the production of the oligomer probe array according to another embodiment of the invention shown in FIG. 5.
Figure 13B:
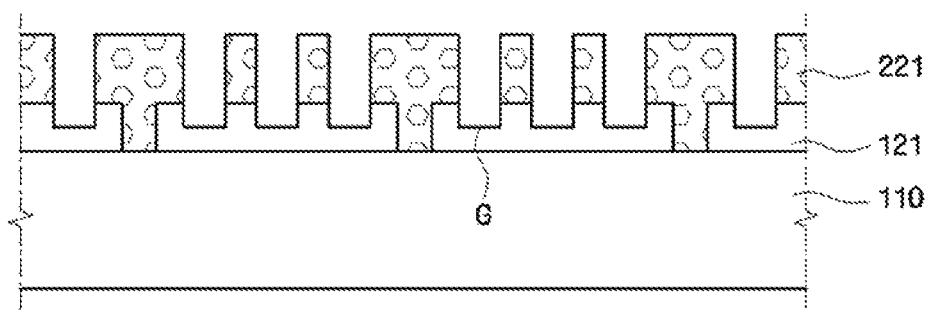

FIGS. 13A and 13B are sectional views of structures at the middle steps of a procedure which illustrates the production of the oligomer probe array according to an embodiment of the present invention shown in FIG. 5.

With reference to FIG. 13A, after an immobilization layer 121a is patterned by the same procedure as FIGS. 8A to 8E, a photoresist film 220 is applied and exposed using a photomask 430 which defines a groove (G) pattern.

With reference to FIG. 13B, after the exposed photoresist film 220 is developed to form a photoresist pattern 221 which defines the groove (G) pattern, an etching process is performed using the photoresist pattern as an etching mask to complete the production of a probe cell region 121 having a three-dimensional surface due to grooves (G) formed therein.

A better understanding of the present, invention may be obtained in light of the following Experimental examples.

Experimental Example 1

Production of a Probe Cell Region Coupled with Nano Particles

A siloxane resin which had a thickness of 90 nm and contained the $(CH_2)_{10}$—OH group was formed on a silicon substrate using a spin coating process, and baked at 250° C. for 60 sec. A photoresist film having a thickness of 3.0 µm was formed on the substrate using the spin coating process, and then baked at 100° C. for 60 sec. The photoresist film was exposed in a projection exposing device having a wavelength of 365 nm using a checkerboard-type dark tone mask having a pitch of 1.0 µm, and then developed with the 2.38% tetramethylammonium hydroxide aqueous solution to form the checkerboard-type photoresist pattern where the regions of length-wise and width-wise straight lines crossing each other were exposed. The immobilization layer was etched using the photoresist pattern as the etching mask to perform patterning, thereby forming the probe cell region.

After 10 ml of a suspension solution of silica beads (Bangs Laboratory, Inc.) that had a diameter of 490 nm and contained OH as the functional group was dispensed on the substrate, spin coating was performed at 50 rpm for 60 sec, washing was performed with IPA (isopropyl alcohol), and curing was performed at 110° C. for 10 min.

Experimental Example 2

Production of a Probe Cell Region

Siloxane which contained the $(CH_2)_{10}$—$NH_2$ group was formed on a silicon substrate to the thickness of 90 nm using a spin coating process, and baked at 250° C. for 60 sec. A photoresist film which contained the $(CH_2)_{10}$—$NH_2$ group and had a thickness of 3.0 µm was formed on the substrate using the spin coating process, and then baked at 100° C. for 60 sec. The photoresist film was exposed in a projection exposing device having a wavelength of 365 nm using a checkerboard-type dark tone mask having a pitch of 1.0 µm, and then developed with the 2.38% tetramethylammonium hydroxide aqueous solution to form the checkerboard-type photoresist pattern where the regions of length-wise and width-wise straight lines crossing each other were exposed. The immobilization layer was etched using the photoresist pattern as the etching mask to perform patterning, thereby forming the probe cell region.

Polystyrene beads (Polyscience. Inc.) that had the COOH group as the functional group and a diameter of 914 nm were used as the nano particles. After the deionized suspension solution of 6.4 mmol of the nano particles, 3.1 mmol of 1-ethyl-3-(3-dimethylaminopropyl) carbodiimide, and 13.1 mmol of N-hydroxysuccinimide was dispensed, spin coupling was performed at 50 rpm for 60 sec, washing was performed with IPA (isopropyl alcohol), and curing was performed at 110° C. for 10 min.

In Situ Synthesis of an Oilgonucleotide Probe

In situ synthesis of the oilgonucleotide probe on the substrate that included the probe cell region and the cell separation region and was produced in Experimental examples 1 to 3 was performed using the photolithography process.

Exposing was performed in a projection exposing device having a wavelength of 365 nm using a binary chromium mask for exposing the desired probe cell region with an energy of 1000 ml/cm² for 1 min to deprotect the end of the linker structure. Subsequently, treatment was performed with an acetonitrile solution which contained amidite-activated nucleotide and tetrazole at a mixing ratio of 1:1 to couple protected nucleotide monomers. Additionally, treatment was performed using a THF solution which contained Ac20, py, and methylimidazole at a mixing ratio of 1:1:1 and a 0.02 M iodine THF solution to conduct capping and oxidation processes.

The above-mentioned deprotection, coupling, capping, and oxidation processes were repeated to synthesize oligonucleotide probes having different sequences with respect to different probe cell regions.

Although exemplary embodiments of the present invention have been described, it will be apparent to those skilled in the art that various modifications and changes may be made thereto without departing from the scope and spirit of the invention. Therefore, it should be understood that the above embodiments are not limitative, but illustrative in all aspects.

The oligomer probe arrays according to the embodiments of the present invention are advantageous in that nano particles are fixed to an immobilization layer by covalent bonding to increase a surface area, thereby improving the reaction yield.

What is claimed is:

1. An oligomer probe array comprising:
   a substrate;
   a plurality of immobilization layer patterns on the substrate, which are chemically and physically separated by probe cell separation regions that are exposed regions on the substrate;
   a plurality of nano particles chemically bonded with a surface of the immobilization layer patterns but not bonded to the surface of the probe cell separation regions; and
   a plurality of oligomer probes coupled with surfaces of the nano particles, wherein said immobilization layer patterns comprise a material selected from the group consisting of a silicon oxide film, a silicate, a silicon oxynitride, and a metal oxynitride film, and materials different from that of the substrate.

2. The oligomer probe array of claim 1, wherein the immobilization layer patterns have three-dimensional surfaces that increase the effective surface area of the immobilization layer patterns for bonding to the nanoparticles.

3. The oligomer probe array of claim 1, wherein the nano particles are arranged on the surface of the immobilization layer patterns to form a self assembled single molecular film.

4. The oligomer probe array of claim 1, further comprising linkers having functional groups disposed on surfaces of the nano particles that couple the functional groups with the oligomer probes.

5. The oligomer probe array of claim 1, wherein the surfaces of the nano particles have functional groups which are capable of being coupled with the immobilization layer patterns, and the oligomer probes.

6. The oligomer probe array of claim 5, wherein the functional groups are alcohol, carboxylic acid, or amine groups.

7. The oligomer probe array of claim 1, wherein the nano particles are formed of polystyrene or silica spheres.

8. The oligomer probe array of claim 1, wherein the nano particles are spherical, and from 10 to 1000 nm in diameter.

9. A method of producing an oligomer probe array, the method comprising:
providing a substrate;
forming an immobilization layer on a surface of the substrate;
patterning the immobilization layer to form a plurality of probe cell regions which are chemically and physically separated by probe cell separation regions that are exposed regions on the substrate;
coupling a plurality of nano particles with a surface of the probe cell regions but not to a surface of the probe cell separation regions; and
coupling a plurality of oligomer probes with surfaces of the nano particles,
wherein said immobilization layer is formed of a material selected from the group consisting of a silicon oxide film, a silicate, a silicon oxynitride, and a metal oxynitride film, and materials different from that of the substrate.

10. The method of claim 9, further comprising
forming photoresist walls on the probe cell separation regions before the plurality of nano particles are coupled.

11. The method of claim 9, wherein the plurality of nano particles are coupled with the surface of the immobilization layer to form a self assembled single molecular film.

12. The method of claim 9, further comprising coupling linkers with the surfaces of the nano particles before the oligomer probes are coupled, wherein the oligomer probes are coupled with the surfaces of the nano particles through the linkers.

13. The method of claim 9, wherein the surfaces of the nano particles have functional groups which are capable of being coupled with the immobilization layer, the oligomer probes, and linkers coupled with the oligomer probes.

14. The method of claim 13, wherein the functional groups are alcohol, carboxylic acid, or amine groups.

15. The method of claim 9, wherein the nano particles are formed of spherical polystyrene bead particles or silica.

16. The method of claim 9, wherein the nano particles are spherical, and from 10 to 1000 nm in diameter.

17. An oligomer probe array comprising:
a substrate;
an immobilization layer that comprises functional groups on the substrate, wherein the immobilization layer is divided into a plurality of activated regions and deactivated regions that are exposed regions of the immobilization layer, wherein the plurality of activated regions are chemically separated by the deactivated regions,
a plurality of nano particles chemically bonded with a surface of the activated regions of the immobilization layer but not bonded to the surface of the deactivated regions, wherein the bond is one of an ether bond, ester bond, or a peptide-amide bond, the nano particles comprising functional groups chemically bonded to a surface thereto; and
a plurality of oligomer probes coupled with the functional groups on the surfaces of the nano particles,
wherein the functional groups of the deactivated regions are deactivated by capping group.

18. The oligomer probe array of claim 17, wherein the nano particles are arranged on the surface of the immobilization layer to form a self assembled single molecular film.

19. The oligomer probe array of claim 17, further comprising linkers disposed on surfaces of the nano particles that couple the nano particles with the oligomer probes therethrough.

20. The oligomer probe array of claim 17, wherein the surfaces of the nano particles have functional groups which are capable of being coupled with the activated regions of the immobilization layer, the oligomer probes, and linkers coupled with the oligomer probes.

21. The oligomer probe array of claim 20, wherein the functional groups are alcohol, carboxylic acid, or amine groups.

22. The oligomer probe array of claim 17, wherein the nano particles are formed of polystyrene or silica spheres.

23. The oligomer probe array of claim 17, wherein the nano particles are spherical, and from 10 to 1000 nm in diameter.

24. A method of producing an oligomer probe array, the method comprising:
providing a substrate;
forming an immobilization layer on an entire surface of the substrate, wherein the immobilization layer comprises functional groups on the substrate;
dividing the immobilization layer into a plurality of activated regions and deactivated regions that are exposed regions of the immobilization layer that surround the activated regions, wherein the plurality of activated regions are chemically separated by the deactivated regions, and the functional groups of the deactivated regions are deactivated by a capping group;
chemically bonding a plurality of nano particles with a surface of the activated regions of the immobilization layer but not to the surface of the deactivated regions, wherein the bond is one of an ether bond, ester bond, or a peptide-amide bond, and the nano particles comprise functional groups chemically bonded to a surface thereto; and
coupling a plurality of oligomer probes with functional groups on the surfaces of the nano particles.

25. The method of claim 24, further comprising
forming photoresist walls on an upper side of the immobilization layer.

26. The method of claim 24, wherein the plurality of nano particles are coupled with the surface of the immobilization layer to form a self assembled single molecular film.

27. The method of claim 24, further comprising coupling linkers with the surfaces of the nano particles before the oligomer probes are coupled, wherein the oligomer probes are coupled with the surfaces of the nano particles through the linkers.

28. The method of claim 24, wherein the surfaces of the nano particles have functional groups which are capable of being coupled with the immobilization layer, the oligomer probes, and linkers coupled with the oligomer probes.

29. The method of claim 24, wherein the functional groups are alcohol, carboxylic acid, or amine groups.

30. The method of claim 24, wherein the nano particles are formed of spherical polystyrene bead particles or silica.

31. The method of claim 24, wherein the nano particles are spherical, and from 10 to 1000 nm in diameter.

* * * * *